United States Patent [19]

Lantzsch et al.

[11] Patent Number: 5,756,858
[45] Date of Patent: May 26, 1998

[54] PROCESS FOR THE PREPARATION OF SUBSTITUTED PHENYLACETIC ACID DERIVATIVES AND NOVEL INTERMEDIATES

[75] Inventors: Reinhard Lantzsch; Rainer Fuchs, both of Wuppertal, Germany

[73] Assignee: Bayer Aktiengesellschaft, Leverkusen, Germany

[21] Appl. No.: 413,282

[22] Filed: Mar. 30, 1995

[30] Foreign Application Priority Data

Apr. 5, 1994 [DE] Germany ............... 44 11 667.5

[51] Int. Cl.$^6$ ................................. C07C 43/303
[52] U.S. Cl. ............ 568/592; 568/591; 562/408; 562/409; 562/412; 562/416; 562/418
[58] Field of Search ................. 562/408, 409, 562/412, 416, 418; 568/591, 592

[56] References Cited

U.S. PATENT DOCUMENTS

| | | | |
|---|---|---|---|
| 4,084,061 | 4/1978 | Kanazawa et al. | 560/105 |
| 5,202,500 | 4/1993 | Theis et al. | 568/592 |
| 5,262,383 | 11/1993 | Fischer et al. | |

FOREIGN PATENT DOCUMENTS

| | | |
|---|---|---|
| 0172365 | 2/1986 | Germany. |
| 0173019 | 3/1986 | Germany. |
| 3535128 | 4/1987 | Germany. |
| 0350069 | 1/1990 | Japan. |

OTHER PUBLICATIONS

Chemical Abstract, vol. 53, abstract No. 21791a, (1959).
Derwet abstract to DE 35351, Apr. 2, 1987, Apr. 2, 1987.

*Primary Examiner*—Marianne M. Cintins
*Assistant Examiner*—Dwayne C. Jones
*Attorney, Agent, or Firm*—Sprung Kramer Schaefer & Briscoe

[57] ABSTRACT

The invention relates to novel processes for the preparation of phenyl acetic acid derivatives of the formula (I) some of which are known

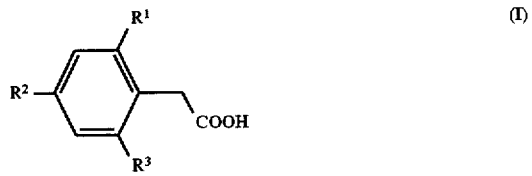

(I)

in which $R^1$, $R^2$ and $R^3$ independently of each other each represent hydrogen, alkyl or alkoxy by ozonolysis of compounds of the formula (II)

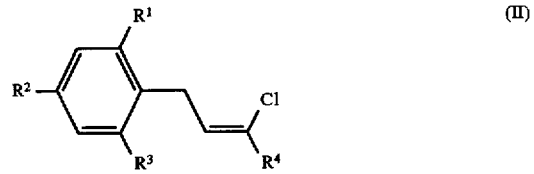

(II)

in which $R^4$ represents hydrogen or methyl and oxidation of the reaction products obtained therefrom. The invention further relates to novel intermediates and a process for the preparation thereof.

2 Claims, No Drawings

PROCESS FOR THE PREPARATION OF SUBSTITUTED PHENYLACETIC ACID DERIVATIVES AND NOVEL INTERMEDIATES

BACKGROUND OF THE INVENTION

1. Field of the Invention

The invention relates to novel processes for the preparation of phenylacetic acid derivatives some of which are known, novel intermediates for their preparation and a process for the preparation thereof.

2. Description of Related Art

It is known that substituted phenylacetic acids and the derivatives thereof are obtained when corresponding substituted aromatics are converted into the chloromethyl or bromomethyl aromatics by chloromethylation or bromomethylation, these are then reacted with cyanides and they are then saponified to give the acid (cf. eg. J. Org Chem 58, Houben-Weyl, Methoden der Organischen Chemie, (Methods in Organic Chemistry) Georg Thieme Verlag, Stuttgart, Volume 5/4 page 484, 1960, Houben-Weyl, Methoden der Organischen Chemie, (Methods in Organic Chemistry) Georg Thieme Verlag, Stuttgart Volume VIII, page 427, 1952). However, this process has the disadvantage that because of the possibility of the carcinogenic bishalogenomethyl ethers formed in the halogenomethylation, increased expenditure on safety precautions is necessary when the reaction is carried out.

It is further known that phenylacetic acids are obtained by carboxylation of benzyl halides under phase transfer conditions (Tetrahedron Lett., 24 (37), 4005-4008; J. Chem. Soc., Chem. Commun. (24), 1090-1091). A considerable disadvantage of these processes, apart from the use of iron carbonyls and cobalt carbonyls is that they must be carried out in part under pressure and lead to reaction mixtures.

SUMMARY OF THE INVENTION

The present invention relates to 1) a process for the preparation of phenylacetic acid derivatives of the formula (I)

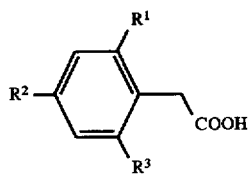

(I)

in which

R$^1$, R$^2$ and R$^3$ independently of each other each represent hydrogen, alkyl or alkoxy, which comprises subjecting substituted phenylpropenes of the formula (II)

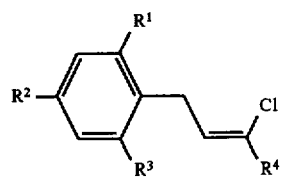

(II)

in which

R$^1$, R$^2$ and R$^3$ have the meaning given above and R$^4$ represents hydrogen or methyl, either a) to an ozonolysis in the presence of inert solvent, then if appropriate isolating the aldehydes of the formula (III) thus obtained

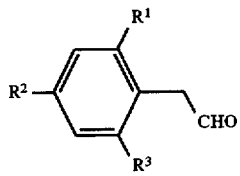

(III)

and then reacting these in the presence of a diluent, in the presence of an acid and in the presence of an oxidizing agent to give the compounds of the formula (I), or b) to an ozonolysis in the presence of alcohols of the formula (IV)

$$R^5\text{—OH} \qquad (IV)$$

in which

R$^5$ represents alkyl, in particular C$_1$–C$_4$-alkyl and very particularly methyl, ethyl or butyl, and if appropriate isolating the phenylacetaldehyde acetals of the formula (V) thus obtained

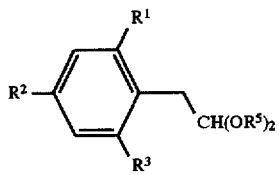

(V)

in which

R$^1$, R$^2$, R$^3$ and R$^5$ have the meaning given above and then reacting these to give the compounds of the formula (I) directly or after hydrolysis to give the aldehydes of the formula (III), in the presence or absence of a diluent in the presence of an acid and in the presence of an oxidizing agent.

2) A process for the preparation of substituted phenylpropenes of the formula (IIa)

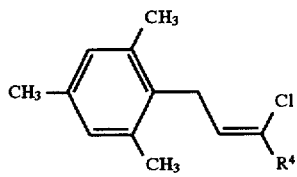

(IIa)

in which

R$^4$ represents hydrogen or methyl, which comprises reacting mesitylene of the formula (VI)

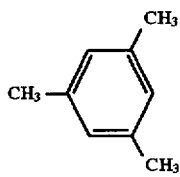

(VI)

with dichloroalkenes of the formula (VII)

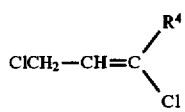
(VII)

in which

R⁴ represents hydrogen or methyl, in the presence or absence of a diluent and in the presence or absence of a catalyst.

3) Novel mesityl acid aldehyde acetals of the formula (Va)

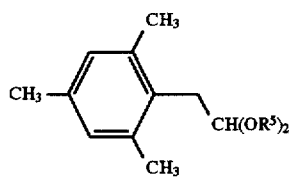
(Va)

in which

R⁵ has the meaning given above. It is considered extremely surprising that the phenylacetic acid derivatives of the formula (I) are obtained virtually quantitatively and in high purity by the process (I) according to the invention by ozonolysis and oxidation, since it is known that the aryl acetaldehydes of the formula (III) formed as intermediates in both process (1a) and process (1b) are very unstable compounds and easily self-react. In addition, arylacetic acids can easily decompose with elimination of $CO_2$. Finally, those skilled in the art would expect further oxidation to give substituted benzoic acid A further advantage of the process according to the invention is that formation is avoided of the highly carcinogenic bishalogenomethyl ether which arises when phenylacetic acid derivatives are prepared by the intermediate stage of chloromethylation of aromatics. The novel process can thus be carried out under considerably improved safety and environmental aspects.

DESCRIPTION OF THE PREFERRED EMBODIMENT

Compounds of the formula (I) in which
R¹, R² and R³ independently of each other each represent hydrogen, $C_1$-$C_4$-alkyl or $C_1$-$C_4$-alkoxy are preferably prepared by the process according to the invention.

Compounds of the formula (I) in which
R¹, R² and R³ independently of each other each represent hydrogen, methyl, ethyl, methoxy or ethoxy are particularly preferably prepared by the process according to the invention.

The general radical definitions or the radical definitions given in preferred ranges listed above apply both to the end products of the formula (I) and to the staring materials or intermediates correspondingly required respectively for their preparation.

These radical definitions can be combined amongst each other and also between the particular ranges and preferred ranges as desired.

If, for example, 1-chloro-3-(2,4,6-trimethylphenyl)-1-propene as starting material, methylene chloride as solvent and ozone are used for the first stage and acetic acid and hydrogen peroxide are used for the second stage, the process (1a) according to the invention may be described by the following formula diagram 1st stage

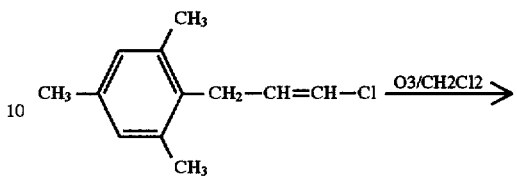

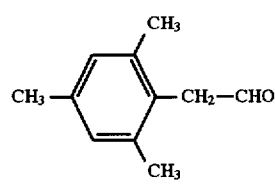

2nd stage

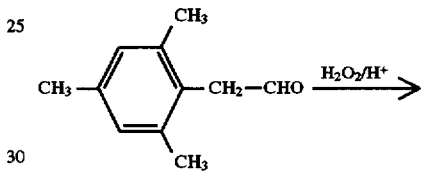

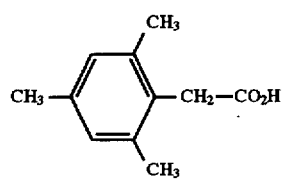

If, for example, 1-chloro-3-(2,4,6-trimethylphenyl)-1-propene and methanol and ozone are used as starting materials for the first stage and acetic acid and hydrogen peroxide are used for the second stage, the process (1b) according to the invention may be described by the following formula diagram:

1st stage

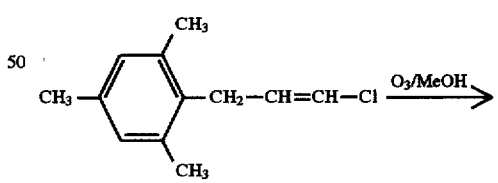

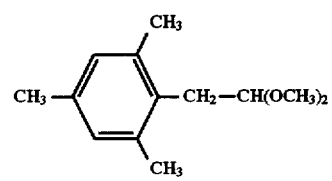

2nd stage

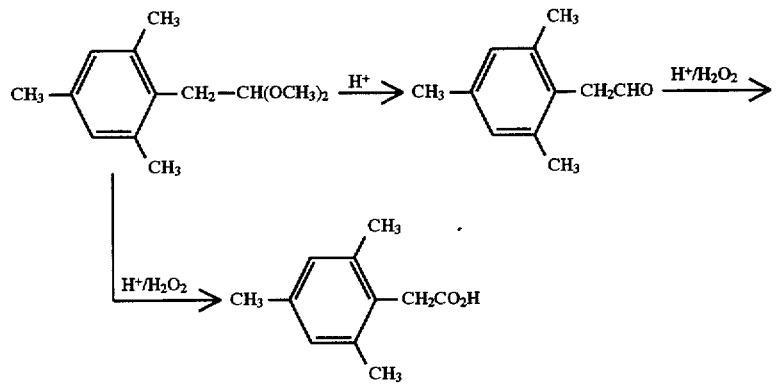

The substituted phenylpropenes to be used as starting materials in the process according to the invention specified above under (1) for the preparation of the compounds of the formula (I) are generally defined by the formula (II). In the formula (II) $R^1$, $R^2$ and $R^3$ preferably or in particular represent that meaning which has already been given above in connection with the description of the compounds of the formula (I) as preferred or in particular preferred, respectively, for $R^1$, $R^2$ and $R^3$. $R^4$ represents hydrogen or methyl.

The compounds of the formula (II) are known or can be prepared by known processes (cf. Comptes Rendus 213, 619–620 (1941)). The known and as yet unknown compounds of the formula (II) can be obtained, for example, by the process according to the invention described under (2).

The alcohols also to be used as starting materials in the process given above under (1b) are generally defined by the formula (IV). In this formula (IV), $R^5$ preferably or preferably has that meaning which has already been given above in connection with the description of the compounds of the formula (IV) as preferred or particularly preferred, respectively, for $R^5$.

The alcohols of the formula (IV) are generally known compounds of organic chemistry.

The phenylacetaldehyde acetals obtainable as intermediates in the process given above under (1b) are generally defined by the formula (V). In this formula (V), $R^1$, $R^2$, $R^3$ and $R^5$ preferably or in particular represent that meaning which has already been given above in connection with the description of the compounds of the formulae (I) and (IV) as preferred or in particular preferred, respectively, for $R^1$, $R^2$, $R^3$ and $R^5$.

Some of the phenylacetaldehyde acetals of the formula (V) have already been disclosed in principle in the literature (cf eg. EP 403 841, FR 2 577 920). The known and the as yet unknown phenylacetaldehyde acetals of the formula (V) can be obtained by the process according to the invention described under (1b).

The aldehydes of the formula (III) further obtainable as intermediates in the process given above under (1) are generally known compounds of organic chemistry.

The process according to the invention described under (1a) is preferably carried out in the presence of a diluent. Diluents which may be used to carry out the process described under (1a) are all conventional organic solvents which are inert under the reaction conditions. These include for example in particular inert solvents: for example chlorinated hydrocarbons such as methylene chloride, ketones such as acetone, esters such as methyl or ethyl acetate and hydrocarbons such as pentane, hexane or cyclohexane.

When the processes according to the invention described under (1a) and (1b) are carried out, the reaction temperatures can be varied within a relatively broad range. Generally, temperatures between −70° C. and +20° C. are employed, preferably between −30° C. and 0° C.

The process according to the invention described under (1b) is preferably carried out in the presence of alcohols. The alcohols which may be used to carry out the process described under (1b) are primary alcohols, in particular methanol, ethanol or n-butanol.

The process according to the invention described under (1a) is carried out in such a way that the appropriate substituted phenylpropene of the formula (II) is introduced into one of the solvents specified above and then ozone is passed in at the specified temperature until the reaction is complete. The excess ozone is blown out with an inert gas, such as nitrogen or argon, or is destroyed with a reducing agent, such as dimethylsulfide or tetrahydrothiophene, the ozonide formed being cleaved at the same time. Instead of sulfides, other reducing agents can alternatively be used, such as thiourea, sodium hydrogen sulfite solution, zinc dust in acetic acid. Cleavage is also achieved by hydrogen by means of catalytic hydrogenation by generally known methods. In addition, the use of amines, such as triethylamine, is possible to cleave the primary ozonide.

The process according to the invention described under (1b) is carried out similarly to the process described above under (1a), but in the presence of alcohols as solvent. The phenylacetaldehyde acetals of the formula (V) are then obtained, which can be converted into the aldellydes of the formula (III) by conventional methods, for example by acid hydrolysis (see Linke in Houben-Weyl, Volume E3, Aldehydes, pages 362–367, 1983).

If appropriate, it can alternatively be advantageous not to isolate the aldehydes of the formula (III) formed by the process (1a) and (1b) according to the invention and the phenylacetaldehyde acetals of the formula (V), but, after distilling off the solvent, to react them further in a one-pot reaction with hydrogen peroxide solution, preferably with addition of acids, such as acetic acid or propionic acid to give the phenylacetic acids of the formula (I) directly.

The phenylacetic acids are obtained by extraction of the aqueous phase or by filtering off.

In the process specified above under (2), mesitylene of the formula (VI) is used as the starting material.

The dichloroalkenes of the formula (VII) also to be used as starting materials in the process specified above under (2) are likewise known synthesis chemicals.

If, for example, mesitylene and 1,3-dichloropropane are used as starting materials and aluminum chloride is used as catalyst, the process (2) according to the invention may be described by the following formula diagram:

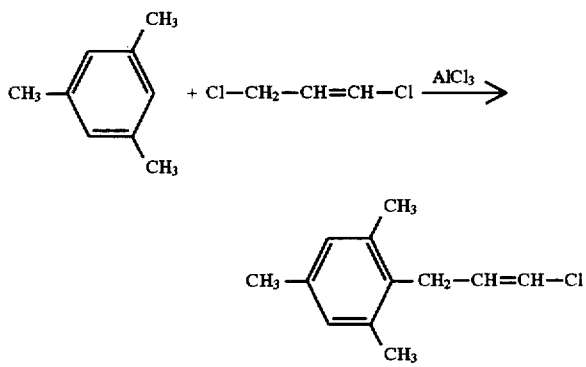

It is considered extremely surprising that the Friedel-Crafts alkylation of mesitylene with 1,3-dichloropropene or dichlorobutene proceeds by the process (2) according to the invention with very good yields of approximately 90% of theory, since in the literature yields of only 10% have been described (Compt. Rendus 213, 619, 1941). An addition to the double bond (Chem. Berichte 66, 1100) or a rearrangement of the methyl groups in mesitylene under the influence of Lewis acids was much rather to be expected.

The process according to the invention thus represents a valuable enrichment of the prior art.

The process according to the invention described under (2) can be carried out in the presence of a diluent:

Diluents which may be used to carry out the process described under (2) include all conventional organic solvents which are inert under the reaction conditions. These include, for example, in particular inert solvents such as pentane, hexane, cyclopentane, cyclohexane, nitroalkanes, carbon disulfide, chlorinated hydrocarbons such as methylene chloride, dichloroethane or tetrachloroethane, nitriles such as acetonitrile, ethers such as diethyl ether, diisopropyl ether, methyl tert-butyl ether, TAME or dimethoxyethane or amides such as dimethylformamaide.

When the process according to the invention described under (2) is carried out, the reaction temperatures can be varied within a relatively broad range. Generally, temperatures between –30° C. and +50° C. are employed, preferably temperatures between –10° C. and +30° C.

The process according to the invention described under (2) is generally carried out at atmospheric pressure. However, it is also possible to employ elevated or reduced pressure.

The process stage according to the invention described under (2) is carried out in the presence of strong acids. Examples of such acids which may be mentioned are: Lewis acids, such as aluminum chloride, aluminum bromide, iron (III) chloride, tin tetrachloride, zinc chloride, titanium tetrachloride or boron trifluoride; mineral acids such as sulfuric acid or hydrochloric acid which can, if appropriate, also be used in the gaseous state and sulfonic acids such as p-toluenesulfonic acid or trifluoromethanesulfonic acid. Aluminum chloride and iron(III) chloride are preferred Per, for example, 1 mol of the compounds of the formula (VII) are used 0.01–30.0 mol %, preferably 0.05–10.0 mol % of Lewis acid, mineral acid or sulfonic acid and 1 to 20 mol of mesitylene in 50–500 ml in one of the abovementioned diluents.

In a preferred embodiment, the process according to the invention described under (2) is carried out in such a way that the mesitylene of the formula (VI), as solvent itself, or in one of the abovementioned solvents, is introduced with a Lewis acid, such as aluminum chloride, then the dichloroalkene of the formula (VII) is added and then the mixture is stirred at the specified temperature until the reaction is complete.

In a further embodiment, the process according to the invention described under (2) is carried out by introducing the dichloroalkenes of the formula (VII) and the mesitylene of the formula (VI), if appropriate in a solvent, then adding a Lewis acid or mineral acid or sulfonic acid and stirring the mixture at the specified temperature until the end of the reaction.

The mixture can be worked up by conventional methods, for example by dilution of the reaction batch with water, extraction with an organic, virtually water-immiscible solvent, drying the organic phase and removing the solvent under reduced pressure. The crude product thus obtained can be purified by distillation.

The mesitylacetaldehydes specified under (3) are generally defined by the formula (Va).

$R^5$ preferably represents $C_1$-$C_4$-alkyl, particularly preferably methyl, ethyl and n-butyl.

The mesitylacetaldehyde acetals of the formula (Va) are novel and subject matter of the invention. They can be obtained by the process (1b) according to the invention. The phenylacetic acid derivatives of the formula (I) to be prepared by the process (1) according to the invention and the substituted phenylpropenes of the formula (IIa) to be prepared by the process (2) according to the invention can be used as starting materials for the preparation of pesticides (cf. eg. EP-A 528 156).

The invention is to be illustrated by the following examples:

EXAMPLES

Example 1

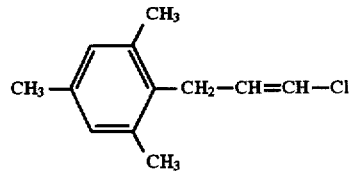

1-Chloro-3-(2,4,6-trimethylphenyl)-prop-1-ene 30 g (0.25 mol) of mesitylene and 0.7 g of aluminum chloride are introduced. 5.55 g (0.05 mol) of 1,3-dichloropropene (cis/trans) are then added dropwise at 20°–25° C. with cooling.

When addition is completed, the mixture is stirred for a further hour at 25° C., is then poured onto 100 ml of ice water and the organic phase is separated off. The aqueous phase is further extracted twice with toluene. The combined organic phases are dried and toluene and excess mesitylene are distilled off under reduced pressure.

12.2 g of 1-chloro-3-(2,4,6-trimethylphenyl)-prop-1-ene (content: 78.0%, GC) are obtained.

After distillation in the Kugelrohr (bulb tube), 8.7 g are obtained (content: GC: 96.9%) corresponding to 87% of theory having a boiling point bp=95°–97° C./1 mbar.

Example 2

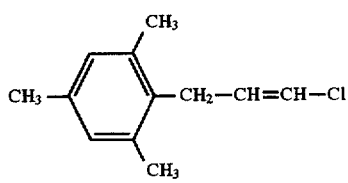

60 g (0.5 mol) of mesitylene and 0.4 g (0.0025 mol) of iron(III) chloride are introduced and stirred for approximately 15 minutes. 11.1 g (0.1 mol) of 1,3-dichloropropene are then added dropwise at 20°–25° C. After complete addition the mixture is continued to be stirred further for approximately 30 minutes, until the gas development is complete.

The mixture is then continued to be stirred for a further 15 minutes at 30° C. The reaction solution is stirred into 250 ml of ice water, the organic phase is separated off and washed with water until it is neutral. After distillation (at approximately 2 mbar) 15.9 g of 1-chloro-3-(2,4,6-trimethylphenyl) prop-1-ene are obtained, which corresponds to a yield of 81.7% of theory.

Example 3

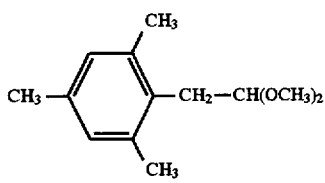

1.95 g (0.01 mol) of 1-chloro-3-(2,4,6-trimethylphenyl) prop-1-ene are dissolved in 60 ml of methanol and cooled to −30° C. Ozone generated by means of an ozone generator is then passed through the reaction mixture in the course of 40 minutes, the clear colorless solution turning light gray. The progress of the oxidation is followed by thin-layer or gas chromatography. After complete conversion, the ozonide formed is cleaved with dimethyl sulfide and the methanol is distilled off in vacuo. The dimethylacetal of the 2,4,6-trimethylphenylacetaldehyde is obtained virtually quantitatively as crude product which can be further purified by distillation in the Kugelrohr (2 mbar, jacket temperature 80°–100° C.), separating off the dimethyl sulfoxide formed from dimethyl sulfide.

The product was characterized by the mass spectrum: m/e =208 (molecular peak), 177, 147, 133, 75 (base peak), 47.

Example 4

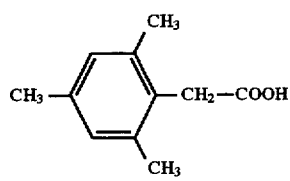

3.5 ml of water, 4 ml of acetic acid and 2 ml of 30% strength hydrogen peroxide are added to the crude product obtained as in Example 3, the dimethylacetyl of 2,4,6-trimethylphenylacetalaldehyde and the mixture is stirred for 12 hours at 25°–35° C. After evaporation to dryness, the residue is taken up in water/ethanol. The product is then filtered off and dried.

1.45 g (81% of theory) of 2,4 6-trimethylphenylacetic acid are obtained having a melting point of 165° C.

Example 5

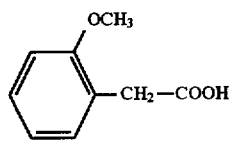

2 g (0.01 mol) of 2-chloro-3-(2'-methoxy-phenyl)-2-butene (disclosed by C.A. 73 (13), 66 192 c) are dissolved in 60 ml of methylene chloride and cooled to −50° C. Ozone generated by an ozone generator is then passed through the reaction mixture in the course of 45 minutes. After the reaction is completed, excess ozone is driven off with nitrogen and 2 g (0.02 mol) of triethylamine are added to the ozonide formed The mixture is allowed to come to room temperature, the organic phase is washed with water and evaporated. 5 ml of glacial acetic acid and, at 60° C., 3 ml of 30% hydrogen peroxide solution are added to the residue and the mixture is stirred for 2 hours. After cooling, the mixture is diluted with water and extracted three times with methylene chloride.

After drying and distillation, 1.5 g (90% of theory) of 2-methoxyphenylacetic acid are obtained having a melting point of 123° C.

We claim:

1. A process for the preparation of phenylacetic acid derivatives of the formula (I)

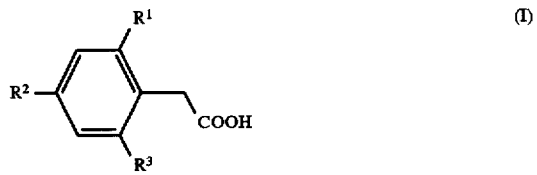

(I)

in which $R^1$, $R^2$ and $R^3$ independently of each other each represent hydrogen, alkyl or alkoxy, which comprises subjecting substituted phenylpropenes of the formula (II)

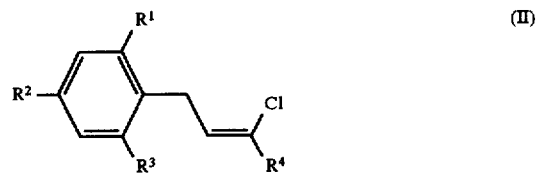

(II)

in which $R^1$, $R^2$ and $R^3$ have the meaning given above and $R^4$ represents hydrogen or methyl, either a) to an ozonolysis in the presence of inert solvents, optionally isolating the aldehydes of the formula (III) thus obtained

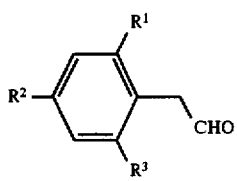 (III)

then reacting these in the presence of a diluent, in the presence of an acid and in the presence of an oxidizing agent to give the compounds of the formula (I), or b) to an ozonolysis in the presence of alcohols of the formula (IV)

 (IV)

in which $R^5$ represents alkyl, and optionally isolating the phenylacetaldehyde acetals of the formula (V) thus obtained

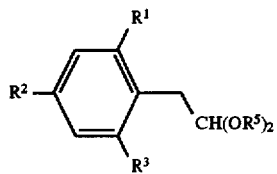 (V)

in which $R^1$, $R^2$, $R^3$ and $R^5$ have the meaning given above and then reacting these to give the compounds of the formula (I) directly or after hydrolysis to give the aldehydes of the formula (III), in the presence or absence of a diluent in the presence of an acid and in the presence of an oxidizing agent.

2. A compound of the formula (Va)

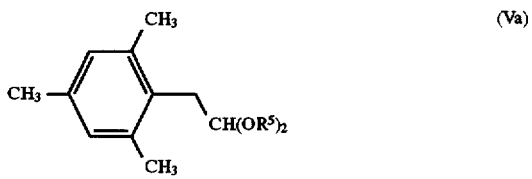 (Va)

in which $R^5$ represents alkyl.

* * * * *